US009623195B2

(12) United States Patent
Liversidge (10) Patent No.: US 9,623,195 B2
(45) Date of Patent: Apr. 18, 2017

(54) NEEDLE ASSEMBLY HAVING SLIDABLE COLLAR TO CONTROL RADIAL ENGAGEMENT OF SLEEVE SEGMENTS WITH INJECTION PEN THREADS (71) Applicant: Barry Peter Liversidge, Colchester (GB)

(72) Inventor: Barry Peter Liversidge, Colchester (GB)

( * ) Notice: Subject to any disclaimer, the term of this patent is extended or adjusted under 35 U.S.C. 154(b) by 556 days.

(21) Appl. No.: 14/161,418

(22) Filed: Jan. 22, 2014

(65) Prior Publication Data
US 2014/0221935 A1 Aug. 7, 2014

Related U.S. Application Data (63) Continuation of application No. 13/061,028, filed as application No. PCT/GB2009/051094 on Aug. 28, 2009, now abandoned.

(30) Foreign Application Priority Data

Aug. 29, 2008 (GB) .................................. 0815748.9

(51) Int. Cl.
*A61M 5/34* (2006.01)
*A61M 5/32* (2006.01)
(52) U.S. Cl.
CPC .......... *A61M 5/347* (2013.01); *A61M 5/3245* (2013.01); *A61M 2005/3254* (2013.01)
(58) Field of Classification Search
CPC . A61M 5/3271; A61M 5/3243; A61M 5/3202
See application file for complete search history.

(56) References Cited

U.S. PATENT DOCUMENTS 2,874,981 A 2/1959 Sherwood
3,667,465 A * 6/1972 Voss .................... A61M 31/007
604/197

(Continued)

FOREIGN PATENT DOCUMENTS

EP 0351541 1/1990
EP 0903156 3/1999
FR 2716113 8/1995

OTHER PUBLICATIONS

International Search Report and Written Opinion for PCT/GB2009/051094 dated Nov. 26, 2009.

*Primary Examiner* — Andrew Gilbert
*Assistant Examiner* — Matthew A Engel
(74) *Attorney, Agent, or Firm* — Grossman Tucker Perreault & Pfleger, PLLC (57) ABSTRACT A needle assembly for an injection pen (22) has a sleeve (21) supporting internally a double-ended needle having an injection end and a non-injection end (25). The end of the sleeve surrounding the non-injection end (25) of the needle is divided into deformable segments (28) and is internally threaded for interengagement with a threaded boss (23) of the injection pen (22). A collar (29) is mounted on the sleeve (21) for sliding movement between a first position where the collar (29) overlies the segmented end and maintains interengagement of the threads at that end with those of the injection pen boss (23) and a second position where the segments may expand radially to come free of the injection pen boss (23). The needle may be mounted on a carrier (68) slidable with respect to the sleeve (21), the carrier (68) being coupled to the sleeve (21) for movement thereby.

9 Claims, 10 Drawing Sheets (56) References Cited

U.S. PATENT DOCUMENTS

| | | | |
|---|---|---|---|
| 4,613,329 A * | 9/1986 | Bodicky | A61M 25/0111 356/139.01 |
| 4,643,199 A * | 2/1987 | Jennings, Jr. | A61M 5/3243 600/576 |
| 4,790,827 A * | 12/1988 | Haber | A61M 5/3243 600/576 |
| 4,813,426 A * | 3/1989 | Haber | A61M 5/322 600/576 |
| 4,841,985 A * | 6/1989 | Wanamaker | A61B 5/15003 600/576 |
| 4,927,019 A | 5/1990 | Haber et al. | |
| 5,030,209 A * | 7/1991 | Wanderer | A61B 5/15003 604/198 |
| 5,057,088 A * | 10/1991 | Narayanan | A61M 5/3243 604/198 |
| 5,167,640 A * | 12/1992 | Balding | A61M 5/3243 604/192 |
| 5,337,756 A * | 8/1994 | Barbier | A61M 5/322 600/576 |
| 5,437,647 A * | 8/1995 | Firth | A61B 5/411 604/110 |
| 5,472,022 A | 12/1995 | Michel et al. | |
| 5,620,427 A * | 4/1997 | Werschmidt | A61M 39/10 137/516.13 |
| 5,827,232 A * | 10/1998 | Chanoch | A61M 5/31551 604/208 |
| 5,855,839 A * | 1/1999 | Brunel | A61M 5/24 264/524 |
| 6,063,040 A * | 5/2000 | Owen | A61B 5/15003 600/573 |
| 6,186,980 B1 * | 2/2001 | Brunel | A61M 5/3202 604/110 |
| 6,409,702 B1 * | 6/2002 | Hu | A61M 5/322 604/110 |
| 6,458,101 B1 * | 10/2002 | Hu | A61M 5/322 604/110 |
| 6,572,565 B2 * | 6/2003 | Daley | A61B 5/15003 600/573 |
| 6,855,129 B2 * | 2/2005 | Jensen | A61M 5/326 604/110 |
| 6,880,701 B2 | 4/2005 | Bergeron et al. | |
| 7,182,734 B2 * | 2/2007 | Saulenas | A61M 5/3232 600/573 |
| 7,462,168 B2 * | 12/2008 | Stonehouse | A61M 5/326 604/192 |
| 7,699,807 B2 * | 4/2010 | Faust | A61M 5/158 604/157 |
| 7,699,813 B2 * | 4/2010 | Liversidge | A61M 5/31501 604/110 |
| 7,828,778 B2 * | 11/2010 | Liversidge | A61M 5/3205 128/919 |
| 7,892,208 B2 * | 2/2011 | Schnell | A61M 5/158 604/162 |
| 8,016,797 B2 * | 9/2011 | Gratwohl | A61M 5/326 604/163 |
| 8,052,653 B2 * | 11/2011 | Gratwohl | A61M 5/326 604/162 |
| 8,096,977 B2 * | 1/2012 | Ayiyama | A61B 5/15003 128/919 |
| 8,177,745 B2 * | 5/2012 | Brechbuehler | A61M 5/326 604/110 |
| 8,286,936 B2 * | 10/2012 | Kitani | A61M 39/26 251/149.1 |
| 8,337,467 B2 * | 12/2012 | Rimlinger | A61M 5/326 604/198 |
| 2003/0014018 A1 * | 1/2003 | Giambattista | A61M 5/002 604/198 |
| 2004/0034323 A1 * | 2/2004 | Manthey | A61M 5/3243 604/198 |
| 2005/0165353 A1 * | 7/2005 | Pessin | A61M 5/3272 604/110 |
| 2005/0277893 A1 * | 12/2005 | Liversidge | A61M 5/31501 604/198 |
| 2006/0184133 A1 * | 8/2006 | Pessin | A61M 5/3257 604/198 |
| 2006/0189931 A1 * | 8/2006 | Riemelmoser | A61M 5/326 604/198 |
| 2007/0129674 A1 * | 6/2007 | Liversidge | A61M 5/326 604/110 |
| 2007/0173772 A1 | 7/2007 | Liversidge | |
| 2007/0191771 A1 * | 8/2007 | Moyer | A61M 5/158 604/158 |
| 2010/0036325 A1 * | 2/2010 | Liversidge | A61M 5/3271 604/198 |
| 2014/0135707 A1 * | 5/2014 | Suzuki | A61M 5/283 604/198 |

\* cited by examiner

NEEDLE ASSEMBLY HAVING SLIDABLE COLLAR TO CONTROL RADIAL ENGAGEMENT OF SLEEVE SEGMENTS WITH INJECTION PEN THREADS

CROSS REFERENCE TO RELATED APPLICATIONS

The present application is the continuation application of U.S. application Ser. No. 13/061,028, filed Feb. 25, 2011, which application was the U.S. national stage application of international PCT/GB2009/051094, filed Aug. 28, 2009, which international applicaton was published on Mar. 4, 2010 as International Publication No. WO2010/023488A1. The international application claims priority of British Patent Application No. 0815748.9, filed Aug. 29, 2008.

This invention relates to a needle assembly for connection to an injection pen having at its forward end a boss with external threads for receiving a needle assembly.

Injection pens are very widely used for self administration of injections. For example, such pens are used by those suffering diabetes, to inject an appropriate amount of insulin for control of the condition. Such a pen has a chamber for a vial of medicament and a mechanism for ejecting a chosen volume of medicament from the vial through an attached double-ended needle. The needles are used only once and then thrown away; the needle is therefore provided within a mount including a socket with internal screw-threads for threading engagement with a threaded boss provided at the forward end of the pen. The non-injection end of the needle is disposed within the socket such that on threading the mount on to the boss drives the non-injection end of the needle through a membrane at the forward end of the vial, so as to communicate with the medicament within the vial.

The injection end of the needle is protected by way of a sheath which is removed immediately before an injection is to be performed but after the connection of the needle to the pen boss. Once the injection has been performed, the needle is unthreaded from the boss and then disposed of in a suitable manner. The unthreading of the needle from the pen boss exposes the user to some risk of a needle stick injury and is not very easy to perform, since the user will attempt to avoid the injection end of the needle, unlike the situation before an injection has been performed, where the injection end is sheathed and in any event has not been contaminated. In an attempt to reduce the likelihood of a needle stick injury, it is known to provide some kind of protection for the injection end of the needle but the user still has to unthread the used needle from the boss at the forward end of the pen.

The non-injection end of the needle is located within the internally-threaded socket of a needle assembly but the relatively sharp end is accessible to within that socket, both before the needle assembly has been threaded on to a pen boss and subsequently when the needle assembly has been removed by unthreading from the boss. Slightly casual handling of the needle assembly as the unthreading action is completed, so freeing the needle assembly, can result in a needle stick injury from the non-injection end of the needle.

Is it is a principal aim of the present invention to provide a needle assembly for use with an injection pen, which facilitates the removal of a used needle assembly from the pen and which, in its preferred aspects, enhances the protection of the non-injection end of the needle, following removal of the assembly from an injection pen.

According to this invention, there is provided a needle assembly for connection to an injection pen having a boss with external threads for receiving the needle assembly, comprising:

a sleeve supporting internally a double-ended needle to extend axially of the sleeve, said needle having an injection end and a non-injection end and the sleeve having a radially deformable end provided with at least one internal profile for radial interengagement with the threads of the pen boss such that with full radial inter-engagement the sleeve is securely connected to the injection pen, the needle being orientated with the non-injection end directed towards said deformable end so that on connection of the sleeve to an injection pen, the non-injection end of the needle penetrates a drug reservoir within the pen;

a collar mounted around the sleeve for sliding movement between a first position adjacent the deformable end at which the collar maintains full radial inter-engagement of the profile with the threads of the boss and a second position where the collar is displaced from said end so that radial deformation of said end allows radial disengagement of the profile from the threads whereby the needle assembly may be pulled axially from the boss.

It will be appreciated that with the needle assembly of this invention, the unused needle assembly is connected to the threaded boss at the forward end of an injection pen in the conventional way, by threading the assembly on to the boss. The needle is then unsheathed and the injection performed, again in the conventional way. Following completion of the injection, the needle assembly may be removed from the pen boss simply by gripping the collar and relatively separating the needle assembly and injection pen. Thus, the collar may be pushed forwardly with respect to the rest of the needle assembly, or the injection pen may be pulled rearwardly with respect to the needle assembly. Either action allows the deformable end of the sleeve to expand radially and so free the full engagement of the internal profile at that end of the sleeve from the threaded boss of the injection pen. Continued relative separating force then moves the needle assembly free of the injection pen, without the need for any rotational unthreading action.

Said internal profile is advantageously defined by an internally-threaded portion at the deformable end of the sleeve, the threads of which portion correspond to the external threads formed on the pen boss.

In a preferred embodiment, the radially deformable end has at least one axially-extending slit and preferably two or three such slits, whereby the effective diameter of the deformable end may increase by the divided segments of the end relatively separating. Such relative separation has the effect of enlarging the slits, at the end of the sleeve, with the segments moving in the radial direction. Each segment of the sleeve may be provided internally with a respective profile for interengagement with the threads of the pen boss.

The sleeve could be manufactured such that those segments are normally in a cylindrical formation but may move radially outwardly on being freed by the collar, or are normally in a flared disposition but are moved radially inwardly upon the collar being moved to its first position. In the case of the latter, it would be possible for the needle assembly to be connected to a pen boss by axial relative movement between the needle assembly and an injection pen, whereafter the collar is moved axially relative to the remainder of the needle assembly thereby to close radially the sleeve segments and engage the threaded portions thereof with the injection pen boss. Following this, small relative rotation between the needle assembly and the injection pen may tighten the needle assembly on the boss. In view of the difficulty of performing essentially axial relative movement between the needle assembly and the injection pen, this is not a preferred manner for connecting the needle assembly to the injection pen.

Advantageously, the needle is mounted on a needle hub, which hub is supported internally within the sleeve. In one embodiment, the hub is fixed axially with respect to the sleeve but in an alternate embodiment, the hub is mounted for axial sliding movement with respect to the sleeve. In this case, means may be provided to move the hub following the completion of an injection such that the non-injection end of the needle is moved further into the sleeve, thereby enhancing protection at the non-injection end of the needle.

A shield may be provided on the sleeve for sliding movement between an injection position, where the injection end of the needle is exposed, and a shielding position where the injection end of the needle is covered by the shield. Such protection shields are known in association with medical needles used to perform injections and may be passive, where the shield moves automatically to the shielding position following the completion of an injection, or active where the user has to perform some action to move the shield to its shielding position. Either kind of protection shield may be employed in association with the needle assembly of this invention. In either case, a locking arrangement may be provided to lock the shield in its shielding position, once moved there following completion of an injection.

In a case where a needle hub is provided within the sleeve and is arranged for movement with respect thereto, means may be provided for interconnecting the needle hub and shield. That interconnecting means may serve to slide the needle hub so that the non-injection end of the needle is moved deeper into the sleeve on movement of the shield to its shielding position. Advantageously, a lost motion arrangement may be provided between the shield and needle hub such that the needle hub moves through a smaller axial distance than does the shield, on moving to its shielding position.

In a preferred embodiment of this invention, the shield is integrated with the collar, such that on the shield moving to its shielding position, the radially deformable end of the sleeve may expand radially to allow disconnection from the threaded pen boss of the internal profile at the deformable end of the sleeve. Thus, the sleeve may give active protection to the injection end of the needle, in that it is gripped and pushed forwardly relative to an injection pen to which the needle assembly has been connected and this action then allows the deformable end of the sleeve to expand radially such that the needle assembly may be pulled free of the pen boss. In the alternative, the shield may be separate from the collar and in this case may give passive protection and a separate action is performed to move the collar forwardly and allow the needle assembly to be pulled free of an injection pen boss.

According to another aspect of this invention, there is provided a needle assembly for connection to an injection pen having a boss with external threads for receiving the needle assembly, comprising:
a sleeve having internal threads at one end for threaded engagement with the external threads of an injection pen boss, the sleeve defining at least one guide extending along the length thereof;
a needle carrier slidably supported within the sleeve and having a lug engaged with the guide of the sleeve and projecting from the outer surface of the sleeve, the needle carrier supporting a double-ended needle extending axially within the sleeve; and
a shield slidably supported on the sleeve and being engaged with the projecting part of the needle carrier lug, whereby forward sliding movement of the shield moves the needle carrier forwardly within the sleeve so moving the non-injection end of the needle further from the one end of the sleeve.

With this aspect of the invention, the shield may have a first position where the needle projects from the forward end of the sleeve and a shielding position where the shield has moved forwardly and covers the injection end of the needle. For this arrangement, a lost motion arrangement may be provided between the slidably mounted needle carrier and the shield, such that the needle carrier moves through a smaller distance than does the shield, on moving from its first position to its shielding position. In this way, when in its shielding position the injection end of the needle will be covered by the shield and the non-injection end of the needle will be moved deeper into the sleeve to enhance the protection of that needle end.

By way of example only, several specific embodiments of needle assembly for an injection pen and arranged in accordance with this invention will now be described in detail, reference being made to the accompanying drawings in which.

The first embodiment of needle assembly for use with an injection pen is shown in FIGS. 1 to 7. This needle assembly comprises a sleeve 21 within which is supported a needle mount (not shown) carrying a double-ended needle (also not shown) of a conventional form and having an injection end able to project from the forward end of the sleeve 21 and a non-injection end disposed within the rearward end of the sleeve. The non-injection end of the needle penetrates a membrane at the forward end of a vial of medicament carried within an injection pen such as that shown at 22, when the needle assembly has been threaded on to a threaded boss 23 provided at the forward end of the pen. The sleeve 21 at its forward end has a retractable shield 24 which may be slid rearwardly towards the pen once the assembly has been mounted thereon, to expose the injection end of the needle, ready for performing an injection.

The above features of an injection pen and needle assembly are well known and form no part of this invention; as such they will not be described in further detail here.

Figure 1:
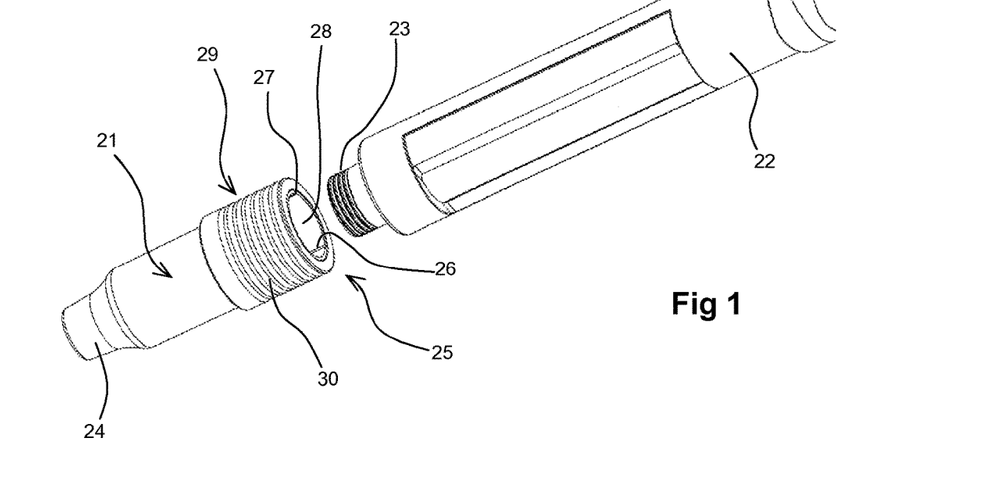
FIG. 1 is an isometric view of a first embodiment of needle assembly, shown in association with the forward end of an injection pen.

The non-injection end region 25 of the sleeve 21 is provided with three slits 26 extending axially from the end face 27 of the sleeve such that the end region is divided into three similar segments 28. Each segment is formed internally with a portion of a thread which corresponds to the thread on the boss 23 of the pen. In its normal condition, the segments all lie on a common cylindrical surface, though each segment may be deformed radially outwardly such that the end region 25 of the sleeve has a greater diameter than when the segments lie on a common cylindrical surface, in the normal condition of the segments.

Figure 3:
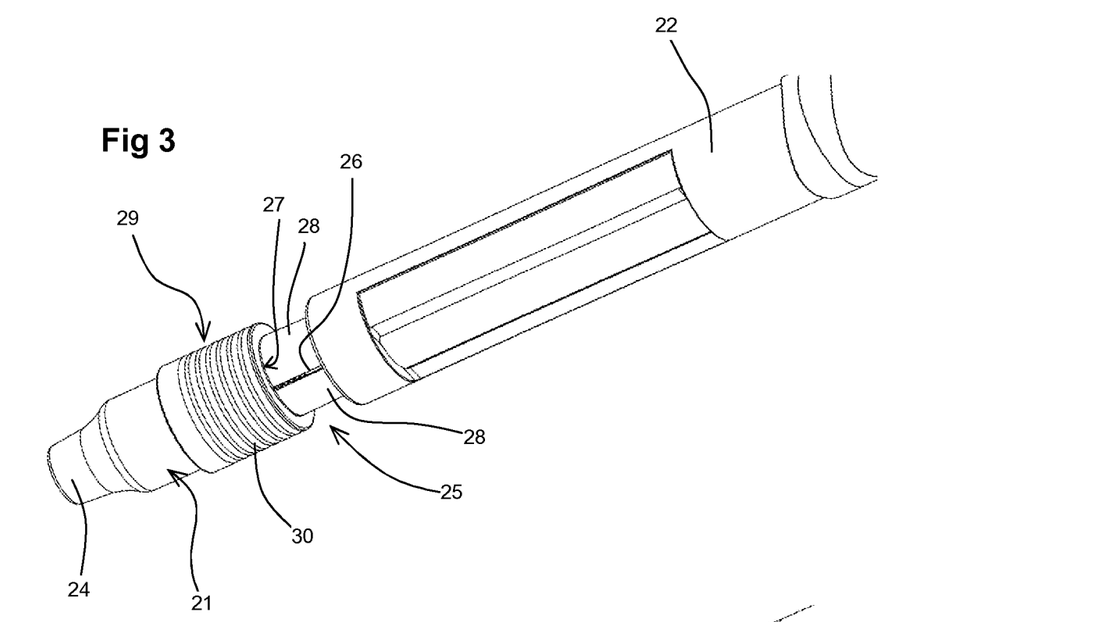
FIG. 3 shows the first stage of the removal of the needle assembly of FIGS. 1 and 2 from the pen.

A collar 29 is slidably mounted on the external surface of the sleeve 21 and may be slid between a first position shown in FIG. 1, where the collar surrounds the segments 28, and a second position shown in FIG. 3 where the collar is free of the segments 28, so allowing the non-injection end region 25 to expand radially. The collar 29 is provided with external ribs 30 to assist gripping of the collar by the fingers of a user and the movement of the collar from its first position to its second position.

Figure 5:
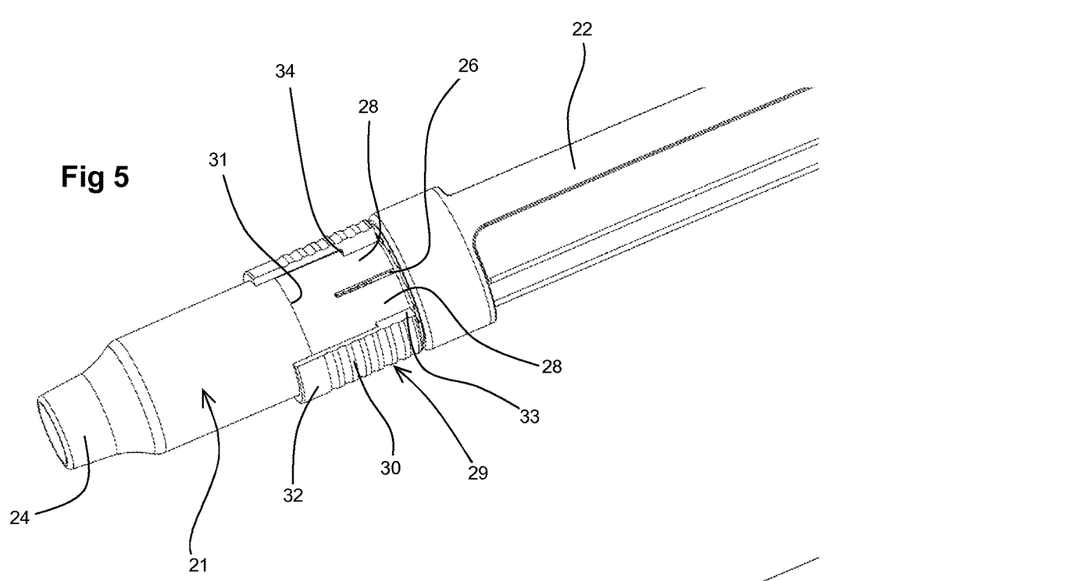
FIGS. 5 and 6 are further isometric views corresponding to those of FIGS. 2 and 4, but partially cut away for clarity.
Figure 6:
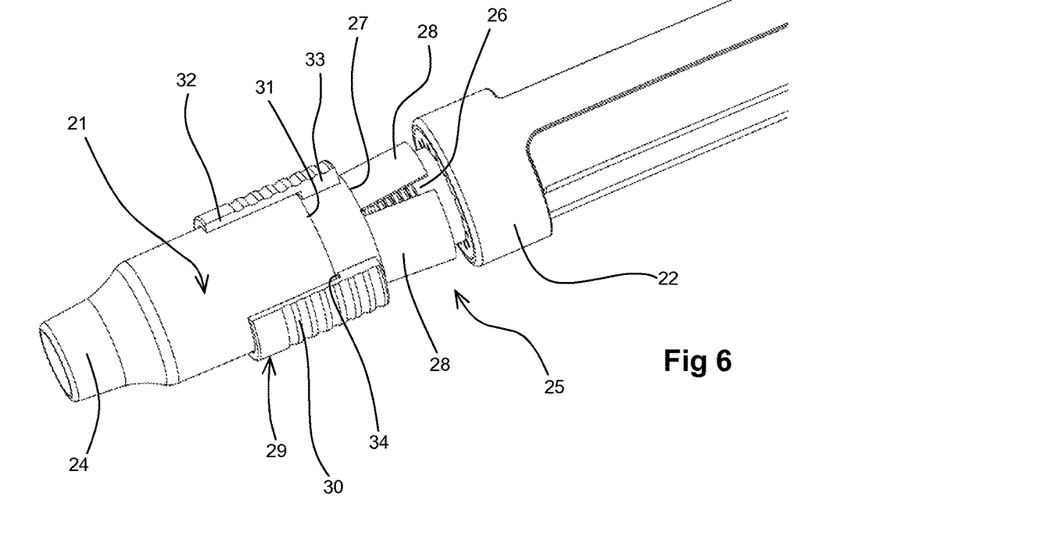

The external diameter of the end region 25 of the sleeve is slightly smaller than the main part of the sleeve, a shoulder 31 being formed between the end region and the main part (FIGS. 5 and 6). Internally, the collar 29 has a forward portion 32 which is a sliding fit on the main part of the sleeve and a rear portion 33 which is a sliding fit on the end region 25 of the sleeve. A corresponding abutment surface 34 is formed between the forward and rear portions of the collar which abutment surface engages the shoulder 31 of the sleeve when the collar is moved to its second position (FIG. 8).

Figure 2:
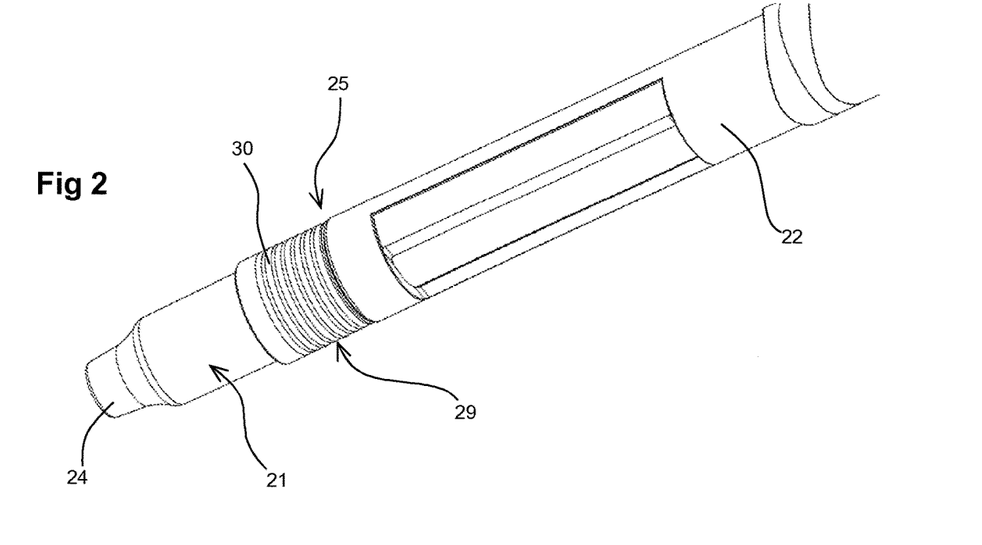
FIG. 2 shows the needle assembly of FIG. 1 connected to the pen.

FIG. 1 shows the needle assembly ready for threading on to the threaded boss 23 of an injection pen 22. The needle assembly is connected thereto in the conventional manner by threading the needle assembly on to the boss (as shown in FIGS. 2 and 5), such that the non-injection end of the needle is moved into communication with a vial in the pen and then an injection is performed again in the conventional manner.

Figure 4:
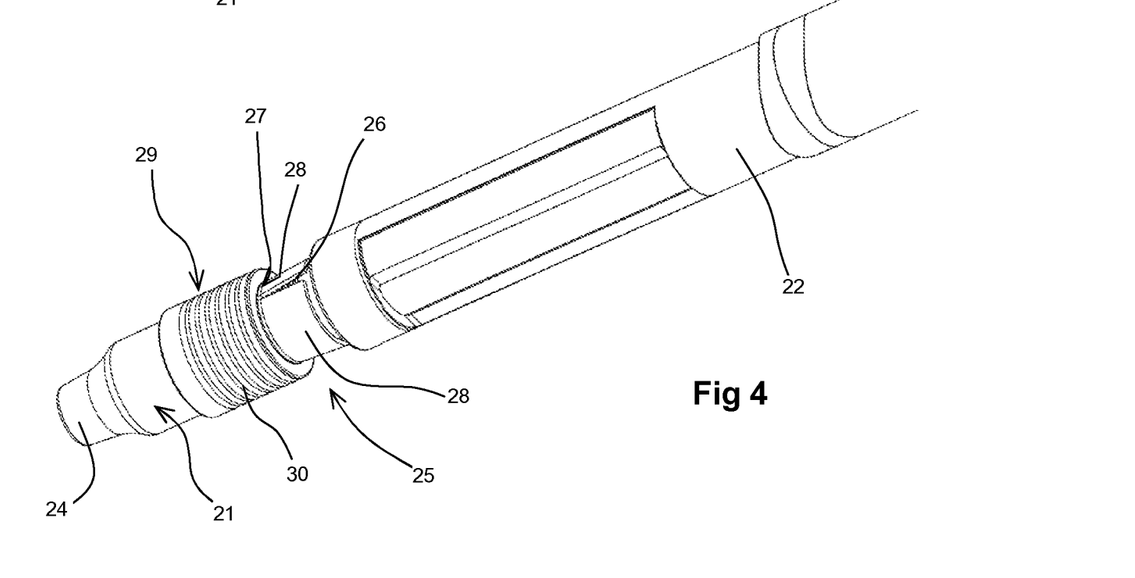
FIG. 4 shows a further stage in the removal of the needle assembly.
Figure 7:
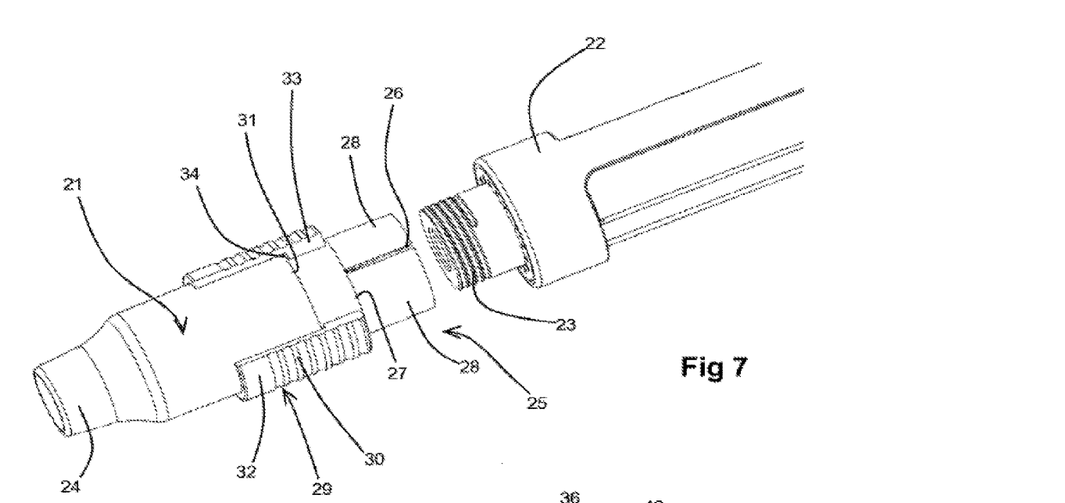
FIG. 7 is an isometric view, again partially cut away for clarity, showing the needle assembly fully removed from the pen injector.

Following completion of the injection, the injection pen is held in one hand while the fingers of a user grip the ribbed part of the collar 29 and the collar is moved axially away from the pen 22, so bringing the abutment surface 34 into engagement with shoulder 31 (FIG. 3). This frees the segments 28 to expand radially as shown in FIGS. 4 and 6 whereafter continued separating force applied to the collar and pen pulls the entire needle assembly away from the boss 23 as shown in FIG. 7. It will be appreciated that removal of the needle assembly may be performed in one smooth forward thrust on the collar 29 relative to the injection pen and wholly obviates the need to unthread the used needle assembly from the injection pen.

Figure 8:
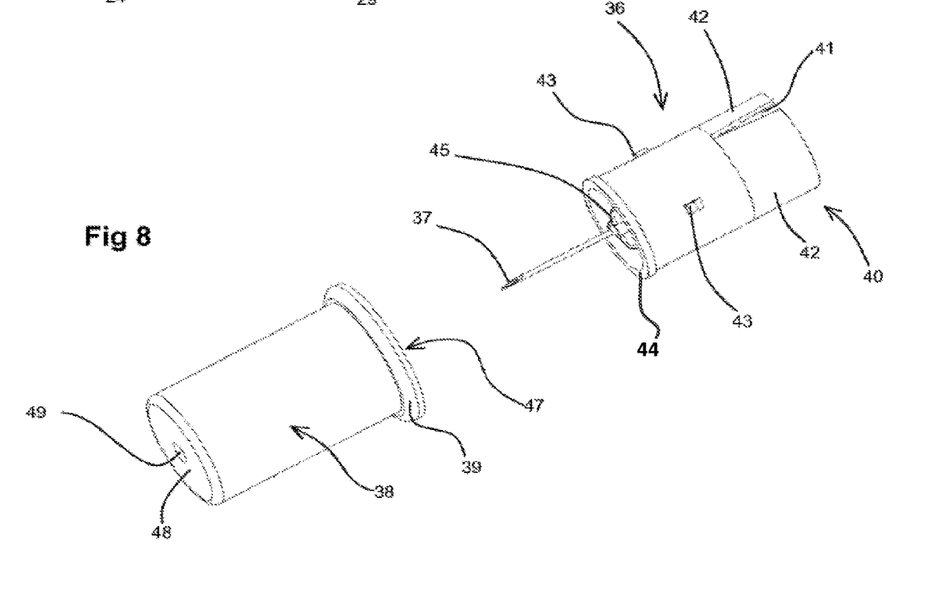
FIG. 8 is an isometric view of a second embodiment of needle assembly including a one-piece collar and protection shield, shown with the shield separated from the assembly sleeve.
Figure 9:
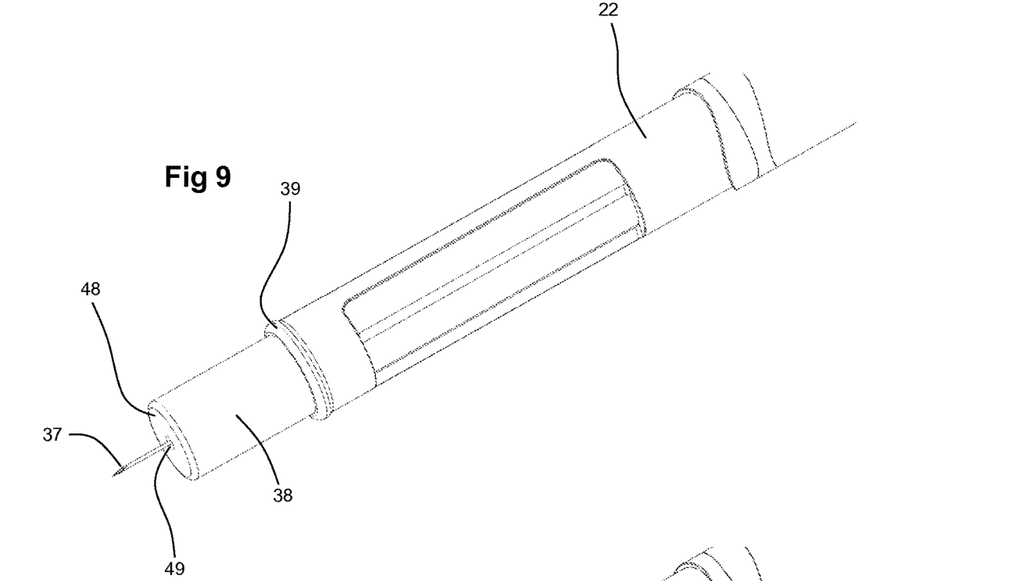
FIG. 9 shows the assembly of FIG. 8 connected to an injection pen, ready for performing an injection.
Figure 10:
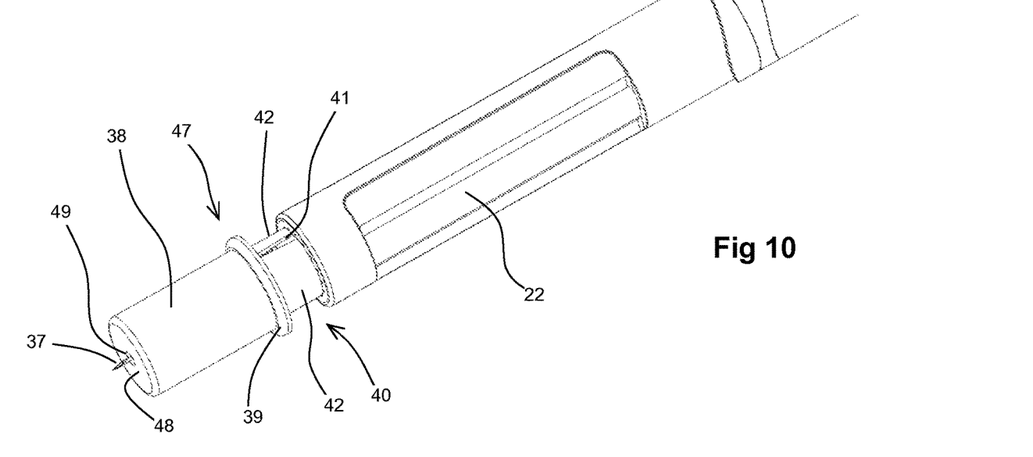
FIG. 10 shows the first stage of the removal of the needle assembly of FIGS. 8 and 9, from the pen.
Figure 11:
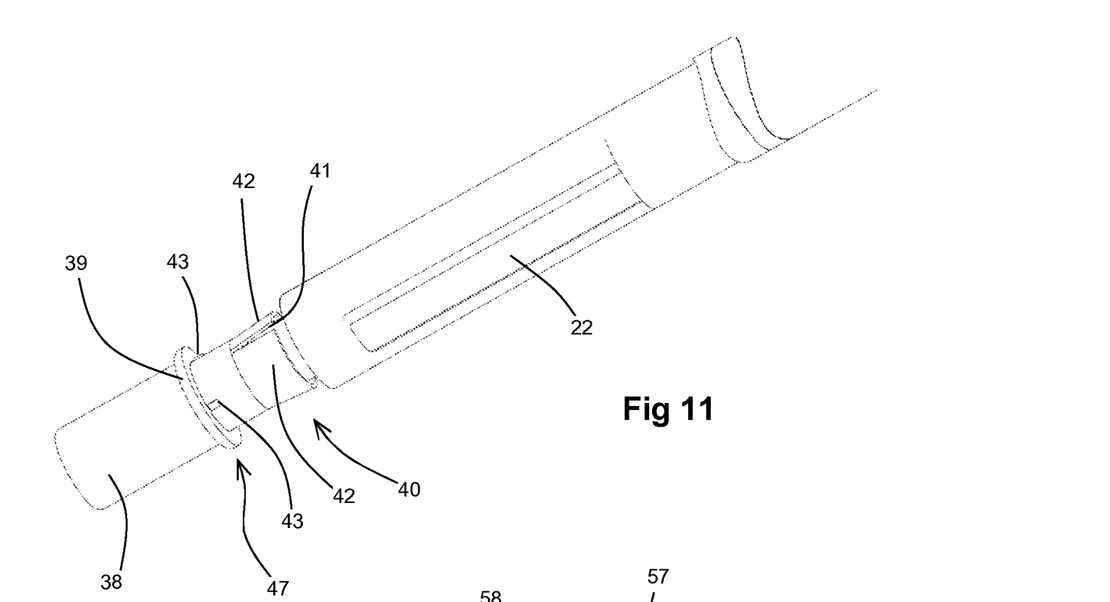
FIG. 11 shows a further stage of the removal of the needle assembly of FIGS. 8 and 9, with the shield locked in its shielding position.

The second embodiment of needle assembly for use with an injection pen is shown in FIGS. 8 to 11. This needle assembly comprises a sleeve 36 carrying a needle 37 and a shield 38 incorporating a unitary collar 39. The sleeve is similarly formed to that described above in relation to the first embodiment and thus has a non-injection end region 40 divided by slits 41 into segments 42, each segment having internal threads and normally lying on a common cylindrical surface, as shown in FIG. 8. Three projecting locking nibs 43 are provided externally on the main part of the sleeve, partway along the length thereof and a rib 44 is formed at the forward end of the sleeve.

Internally, the sleeve has a hub 45 which supports a double-ended needle, the injection end of the needle being shown in FIG. 8 and the non-injection end being disposed within end region 40 of the sleeve.

The shield 38 has its rearward end 47 to be a close sliding fit on the external surface of the sleeve and the greater part of the internal surface of the shield being a sliding fit on the rib 44 of the sleeve. At its forward end, the shield has a radial end face 48 formed with a central hole 49 for the needle 37.

In use, the needle assembly is fitted to an injection pen 22 with the shield in its rearward position where the rear end of the shield is essentially co-planar with the rear end of the sleeve, by threading the needle assembly on to the boss 23. Though not shown in FIG. 9, a sheath would extend over the needle during this action. Following de-sheathing of the needle and the performance of an injection, the assembly is removed by thrusting the shield 38 forwardly (FIG. 10) so taking the collar 39 clear of the non-injection end region 40 of the sleeve. A continued forward thrust on the shield 38 brings the rearward end 47 of the shield 38 into engagement with the rib 44 at the forward end of the sleeve, with the rearward end of the sleeve forwardly of the nibs 43. The shield is thus looked in its forward position, shielding the needle and allowing radial enlargement of the non-injection end region of the shield 38 (FIG. 11), such that a continued forward thrust on the shield pulls the needle assembly clear of the injection pen boss 23.

The third embodiment of needle assembly for use with an injection pen is shown in FIGS. 12 to 16. This embodiment is similar to that described with reference to FIGS. 1 to 7 but differs from the first embodiment in that it includes enhanced protection for the non-injection end of the sleeve.

Figure 12:
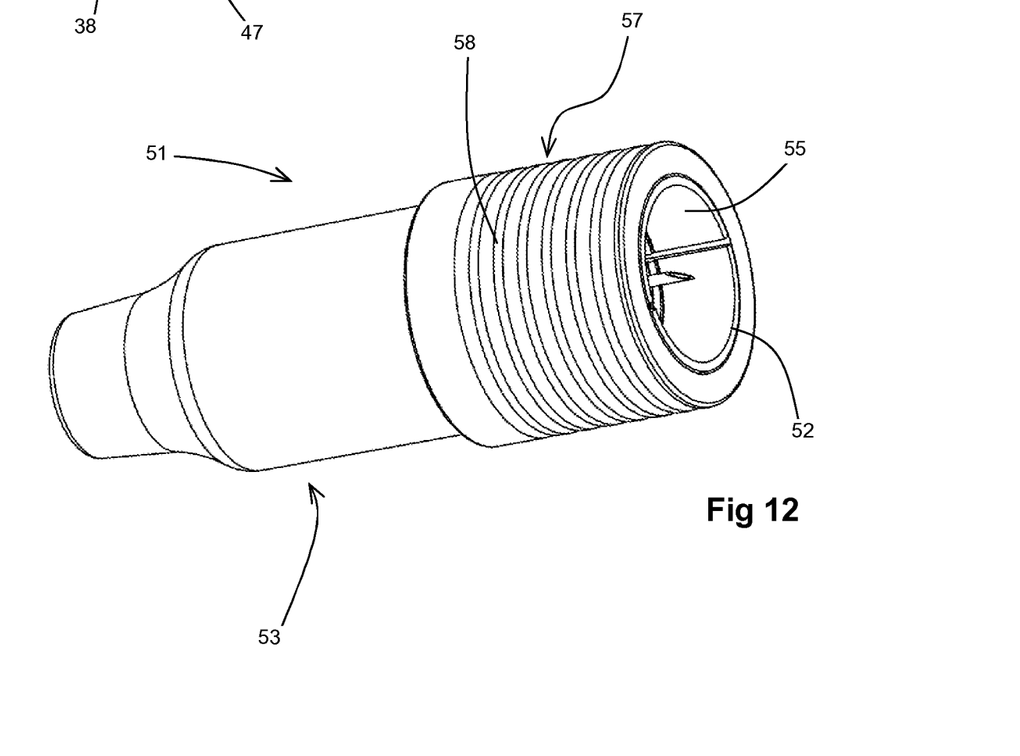
FIG. 12 is an isometric view of a third embodiment of needle assembly including a shield for the non-injection end of the needle.

In this embodiment, the sleeve 51 is formed in two pieces, with a rearward section 52 being slidably received within a forward section 53. The rearward section has its forward end portion formed as a continuous ring 54 slidable within the forward section 53 and the rearward end portion as separate segments 55 corresponding to segments 28 of the first embodiment and thus which may be threadingly engaged with the threaded boss 23 of an injection pen 22. The ring 54 has four externally-projecting nibs 56, for a purpose to be described below.

The rear part of the forward section is formed as a collar 57 having external ribs 58 to facilitate gripping of the collar. A double-ended needle (not shown other than the non-injection end of which, in FIG. 12) is supported on a hub provided internally within the forward section. The forward part of the forward section is similarly formed to that of the first embodiment and so includes a sliding shield which will not be described in further detail here.

Figure 13:
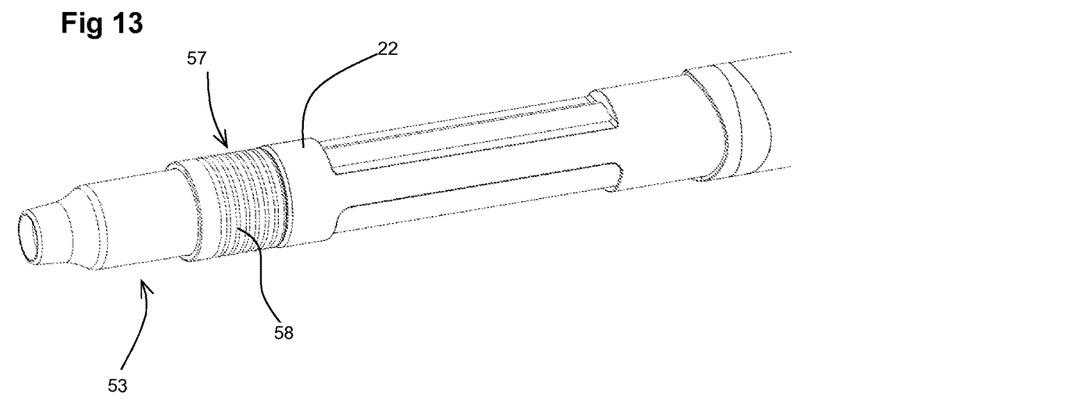
FIGS. 13, 14 and 15 respectively show the connection of the needle assembly of FIG. 12 to an injection pen, and the first and second stages of the removal of that needle assembly from the injection pen following the performance of an injection.
Figure 14:
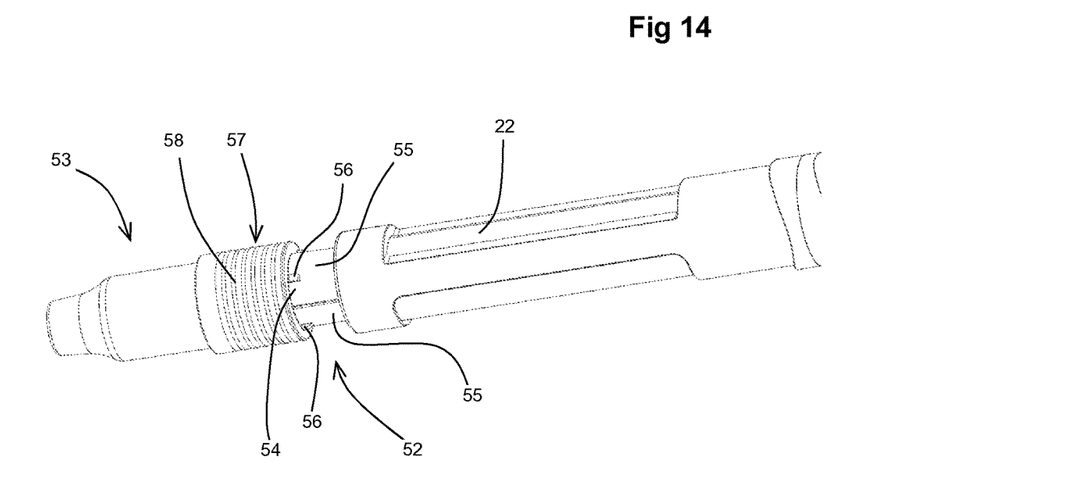

In use, the needle assembly is initially as shown in FIG. 12, with the collar 57 closely encircling the segments 55 and so preventing radial enlargement of the rear end region of the rearward section 52 of the sleeve. The needle assembly is threaded on to the pen boss 23 in the conventional way as shown in FIG. 13 and an injection performed as described above. Following completion of the injection, the collar 57 is gripped and is thrust forwardly relative to the injection pen, so sliding the forward section 53 forwardly relative to the rearward section 52. Eventually, the position shown in FIG. 14 is reached where the nibs 56 engage behind the rear face of the forward section 53 of the sleeve and prevent rearward movement of the forward section relative to the rearward section. In effect, this action pulls the rearward section rearwardly relative to the forward section and so also rearwardly relative to the non-injection end of the needle, thus enhancing protection to that non-injection end.

Figure 15:
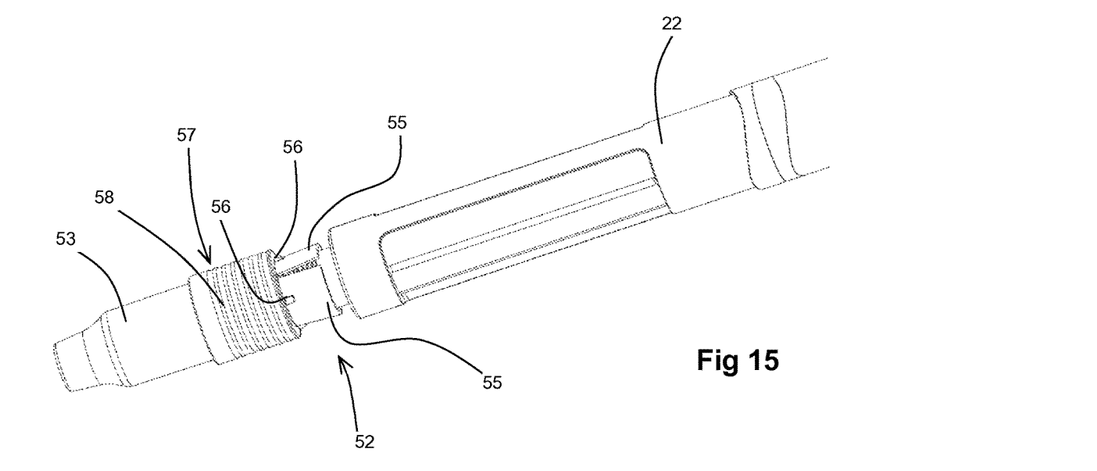
Figure 16:
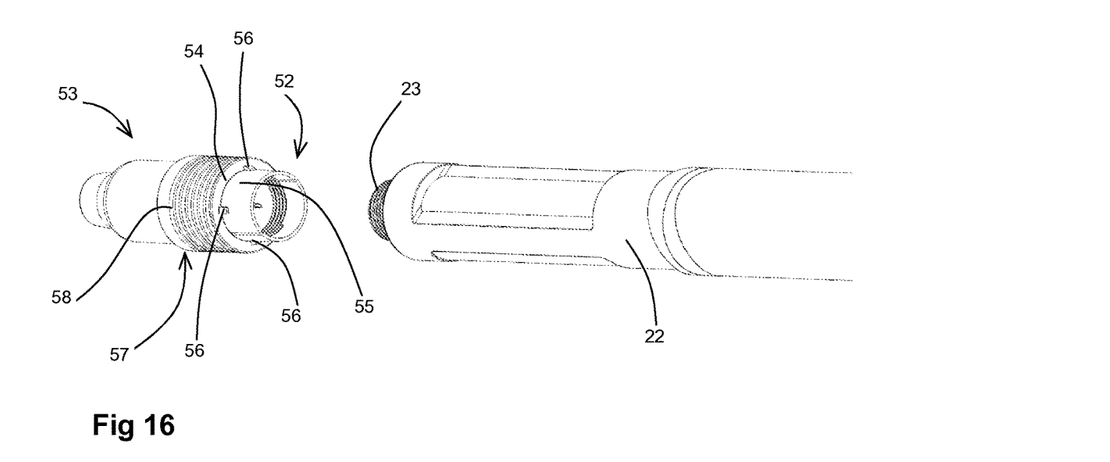
FIG. 16 shows the needle assembly of FIGS. 12 to 15, following complete removal from an injection pen.

Once the position of FIG. 14 has been reached, continued forward thrusting of the collar 57 relative to the pen 22 allows the segments to expand radially as shown in FIG. 15 and so allow the needle assembly to come free of the boss 23 without the need to unthread the sleeve from the pen. FIG. 16 shows the needle assembly thus separated and with the rearward section 52 of the sleeve locked in its position extended out of the forward section 53.

The fourth embodiment of needle assembly for use with an injection pen is shown in FIGS. 17 to 20. This needle assembly comprises a sleeve 60 having a rearward end 61 internally threaded for connection to a threaded boss at the forward end 62 of an injection pen 63. The sleeve has three equi-spaced slots 64 extending from the forward end face, approximately half way along the length of the sleeve. Externally, the sleeve is provided with three projecting nibs 65.

Figures 17, 18:
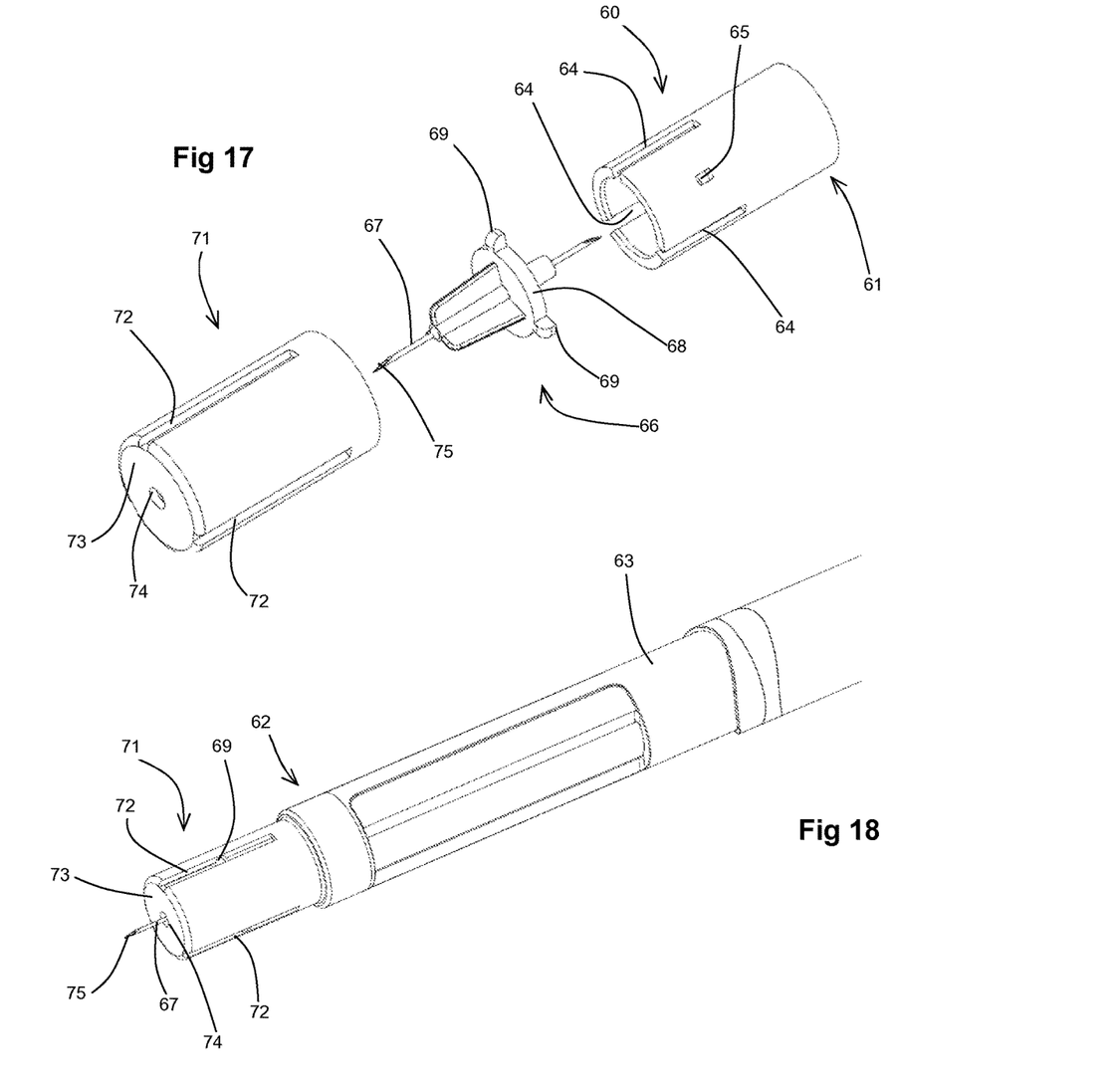
FIG. 17 is an isometric exploded view of fourth embodiment of needle assembly of this invention.
FIGS. 18, 19 and 20 show successive stages in the connection of the needle assembly of FIG. 17 to an injection pen and subsequently the removal of the needle assembly from the pen.
Figure 19:
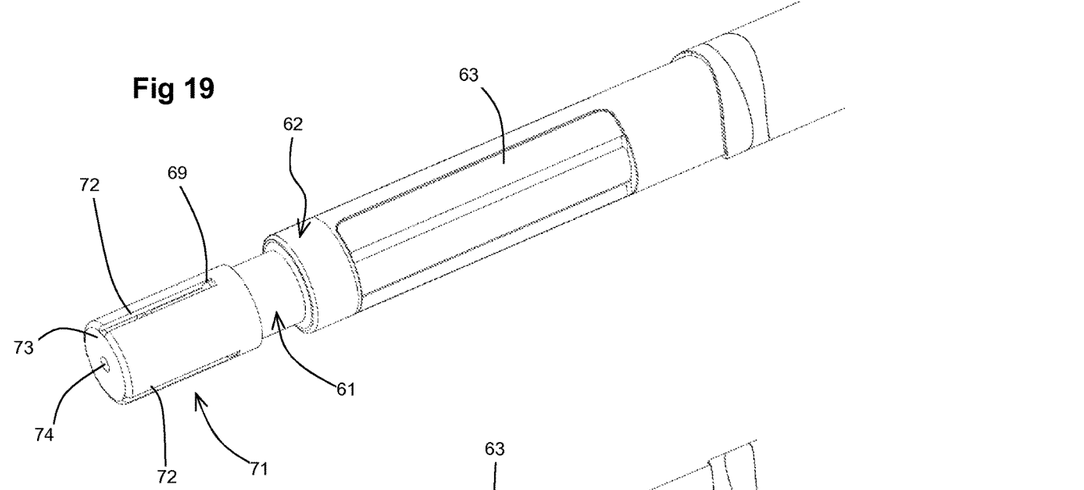
Figure 20:
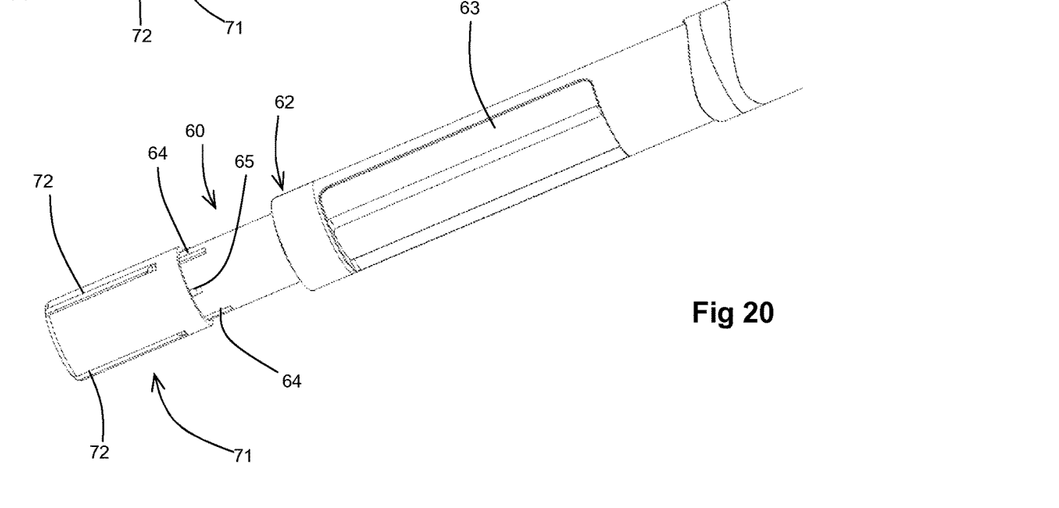

A needle hub 66 supports a double-ended needle 67 the needle hub including an annular carrier 68 provided with three lugs 69 receivable in the slots 64 and when so received, projecting beyond the outer surface of the sleeve.

A shield 71 is slidably carried on the sleeve 60 and has three equi-spaced slots 72 within which the projecting parts of the lugs 69 are received when the shield is assembled to the sleeve. At its forward end, the shield 71 has an end face 73 formed with a central hole 74 through which the injection end 75 of the needle 67 may project when the shield has been moved rearwardly.

The projecting parts of the lugs 69 of the needle hub 66 and the slots 72 of the shield 71 which receive those projecting parts serve as an interconnection means for the shield and needle hub 66. That interconnection means allows relative sliding movement of the shield and hub between limits defined by the configuration of the lugs and slots such that on the projecting parts of the lugs reaching the ends of the slots, continued movement of the shield slides the hub with the shield.

The three components shown in FIG. 17 are assembled together with the shield moved to its rearward position such that the injection end 75 of the needle projects through central hole 74, as shown in FIG. 18, but with a sheath (not shown) over the projecting part of the needle. When in this disposition, the needle assembly is threaded on to an injection pen threaded boss so that the non-injection end of the needle penetrates the end membrane of a vial of medicament within the pen. The needle is unsheathed and the injection performed in the usual way.

Following completion of the injection, the shield 71 is slid forwardly until the closed ends of the slots 72 in the shield engage the lugs 69 whereupon those lugs prevent further forward movement of the shield relative to the sleeve 60. When in this position (FIGS. 19 and 20) the nibs 65 engage behind the rear end face of the shield 71 and so prevent the shield being moved rearwardly, towards the injection pen. Thereafter, the assembly may be unscrewed from the injection pen with the shield remaining locked and so preventing the risk of needle stick injury.

Though not shown in FIGS. 17 to 20, the rearward end 61 of the sleeve 60 may be configured as has been described above with reference to the first to third embodiments. In this case, the rearward end 61 may be formed into two or more segments divided by slits such that the segments may move radially outwardly to increase the effective diameter of the sleeve at the rearward end. The shield, when in its rearward position shown in FIG. 18, may act as a collar for the segments and so prevent radial enlargement of the rearward end of the sleeve. When the shield is gripped and is slid forwardly away from the injection pen, the segments are freed to expand radially and so allow the needle assembly as a whole to be pulled axially away from the injection pen.

What is claimed is:

1. A needle assembly for connection to an injection pen having a boss with external threads for receiving the needle assembly, the needle assembly comprising:
   a sleeve having internal threads at one end for threaded engagement with the external threads of an injection pen boss, the sleeve defining at least one guide extending along a length thereof;
   a needle carrier slidably supported within the sleeve and having a lug engaged with the guide of the sleeve and projecting from the outer surface of the sleeve, the needle carrier supporting a double-ended needle extending axially within the sleeve; and
   a separate shield slidably supported on the sleeve and being engaged with a projecting part of the lug, whereby forward sliding movement of the shield moves the needle carrier forwardly within the sleeve, so moving a non-injection end of the needle further from said one end of the sleeve;
   wherein said one end of the sleeve is formed into two or more divided segments and the shield is mounted on the sleeve for sliding movement between a first position at which the shield maintains full radial engagement of the two or more divided segments with the external threads of the injection pen boss, and a second position where the shield is displaced from said one end so that radial disengagement of the external threads is possible by radial deformation of the two or more divided segments at said one end.

2. The needle assembly as claimed in claim 1, wherein the shield is provided with a groove extending along the length thereof and in which the projecting part of the lug is engaged whereby the needle carrier moves through a smaller distance than the shield, upon the shield moving from an injection position to a shielding position.

3. The needle assembly as claimed in claim 1, wherein an internal profile is defined by an internally-threaded portion at said one end of the sleeve corresponding to the external threads formed on the boss of the injection pen.

4. The needle assembly as claimed in claim 3, wherein there is at least one generally axially-extending slit in a wall of the sleeve at a deformable end whereby an effective diameter of the deformable end may increase by enlargement of the slit.

5. The needle assembly as claimed in claim 4, wherein there is a plurality of generally axially-extending slits in the wall of the sleeve at said deformable end thereby dividing said deformable end into a plurality of segments.

6. The needle assembly as claimed in claim 5, wherein each of the plurality of segments are provided internally with a respective profile for interengagement with the external threads of the boss of the injection pen.

7. The needle assembly as claimed in claim 1, wherein the needle is mounted on a needle hub and the needle hub is supported internally within the sleeve.

8. The needle assembly as claimed in claim 7, wherein the needle hub is mounted within the sleeve for axial sliding movement with respect thereto.

9. The needle assembly as claimed in claim 1, wherein there is provided the shield mounted on the sleeve for sliding movement between an injection position where the injection end of the needle is exposed and a shielding position where the injection end of the needle is covered by the shield.

* * * * *